United States Patent [19]
Giannessi et al.

[11] Patent Number: 6,127,552
[45] Date of Patent: Oct. 3, 2000

[54] PROCESS FOR PRODUCING (R)-3-HYDROXY-4-BUTYROLACTONE USEFUL FOR PREPARING (R)-CARNITINE

[75] Inventors: Fabio Giannessi; Maria Ornella Tinti; Francesco De Angelis, all of Rome, Italy

[73] Assignee: Sigma-Tau Industrie Farmaceutiche Riunite S.p.A., Rome, Italy

[21] Appl. No.: 09/200,852

[22] Filed: Nov. 30, 1998

[30] Foreign Application Priority Data

Dec. 16, 1997 [IT] Italy ................................ RM97A0780

[51] Int. Cl.$^7$ ........................ C07D 307/02; C07D 307/56
[52] U.S. Cl. ............................................. 549/295; 549/326
[58] Field of Search ...................................... 549/326, 295

[56] References Cited

U.S. PATENT DOCUMENTS

| | | | |
|---|---|---|---|
| 5,412,113 | 5/1995 | Giannessi et al. | 549/328 |
| 5,468,881 | 11/1995 | Ebata et al. | 549/326 |
| 5,491,260 | 2/1996 | Giannessi et al. | 562/567 |
| 5,532,409 | 7/1996 | Giannessi et al. | 562/561 |
| 5,532,410 | 7/1996 | Giannessi et al. | 562/567 |
| 5,599,978 | 2/1997 | Giannessi et al. | 562/567 |
| 5,714,619 | 2/1998 | Giannessi et al. | 549/313 |

OTHER PUBLICATIONS

Chemical Abstract vol. 118 No. 168701 Hollingsworth, "Process for the Rep. of 3,4–dihydroxybutanoic acid & salt thereof by alkali peroxide tech. of glucose some" Jan. 1995.

*Primary Examiner*—John Kight
*Assistant Examiner*—Raymond Convington
*Attorney, Agent, or Firm*—Oblon, Spivak, McClelland, Maier & Neustadt, P.C.

[57] ABSTRACT

A process is disclosed for producing (R)-3-hydroxy-4-butyrolactone from its enantiomer, (S)-3-hydroxy-4-butyrolactone. The (R)-enantiomer can be advantageously utilized in several organic synthesis and industrial processes, such as e.g. GABOB and (R)-carnitine preparation.

16 Claims, No Drawings

PROCESS FOR PRODUCING (R)-3-HYDROXY-4-BUTYROLACTONE USEFUL FOR PREPARING (R)-CARNITINE

BACKGROUND OF THE INVENTION

1. Field of the Invention

The present invention relates to a process for producing (R)-3-hydroxy-4-butyrolactone from its enantiomer (S)-3-hydroxy-4-butyrolactone.

2. Description of the Background

Both (S)-3-hydroxy-4-butyrolactone, 1(S), and (R)-3-hydroxy-4-butyrolactone, 1(R), are versatile chiral intermediates useful in several industrial synthesis. Lactone 1(S) is e.g. utilised in the preparation of (S)-oxyracetam, esters of 5,6-dihydroxy-3-ketohexanol and natural-like substances, such as multistriatine. IT 01276207 (Sigma-Tau) discloses a process for producing 1(S) from (S)-carnitine, a cheap waste compound which forms in the preparation of (R)-carnitine (of which several therapeutical utilisations are known) in equimolar amounts with respect to (R)-carnitine. Indeed, the processes most widely utilised to-date for preparing (R)-carnitine are based on the resolution of racemic mixtures. Also EP 513,430 discloses a process for preparing 1(S) from, however, a source of D-hexoses.

The lactone 1(R) can be used for synthesizing β-lactame antibiotics, the known anticonvulsivant GABOB [(R)-4-amino-3-hydroxybutyric acid] and (R)-carnitine. In order to carry out the (R)-carnitine synthesis, lactone 1(R) is first converted to an alkyl-4-halogen-3-hydroxybutyrate (as disclosed e.g. in JP 04149151) which is then converted to (R)-carnitine (see e.g. Zhou, B.; Gopalan, A. S.; Van Meddlesworth, F.; Shieh, W. R.; Sih, C. J., *J. Am. Chem. Soc.* 1983, 105, 5925–5926; Boots, S. G; Boots, M. R.; *J. Pharm. Science*, 1975, 64, 1262–1264).

In spite of its utility as a versatile intermediate, to-date no satisfactorily suitable processes have been provided which allow an industrial scale synthesis to be conducted.

The synthesis from L-ascorbic acid is a 7-step process and its yield is 29% only (Tanaka, A.; Yamashita, K, *Synthesis*, 1987, 570–572), whilst the synthesis from dimethyl-(R)-malate requires a cumbersome reduction step with the borane-dimethylsulfide complex and $NaBH_4$. This reduction step is practically unfeasible on an industrial scale and entails severe safety and pollution problems (Saito, S.; Hasegawa, T.; Inaba, M.; Nishida, R.; Fujii, T.; Nomizu, S.; Moriwake, T., *Chem. Lett.*, 1984,1389–1392).

It would be, therefore, advantageous to have an industrially feasible process for producing (R)-3-hydroxy-4-butyrolactone, which does not present the several serious drawbacks of the known methods: a plurality of steps, low yields, unsatisfactory optical purity, use of expensive, hazardous and/or polluting reactants.

The object of the present invention is to provide such a process which further present the advantage of utilizing the enantiomer of the end compound, i.e. (S)-3-hydroxy-4-butyrolactone, as starting material which, as previously mentioned, can be easily and unexpensively obtained from a waste material such as (S)-carnitine with the process disclosed in IT 01276207.

The process of the present invention is shown in the following reaction scheme:

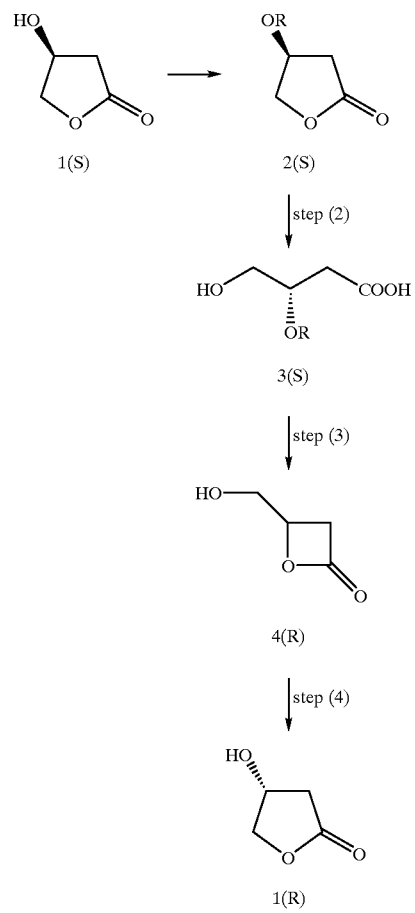

With reference to the previous reaction scheme, the process of the present invention comprises the steps of:

(1) acylating (S)-3-hydroxy-4-butyrolactone, 1(S), to (S)-3-acyloxy-4-butyrolactone, 2(S), wherein —OR is a leaving group wherein R is a group selected from alkylsulfonyl having 1–12 carbon atoms, arylsulfonyl, formyl and trifluoroacetyl, by reacting 1(S) with an acylating agent selected from an acyl halogenide RY and an anhydride R—O—R wherein Y is halogen, preferably chlorine, and R is as previously defined, optionally in the presence of an organic base consisting of a tertiary amine, in an aprotic organic solvent, at molar ratio 1(S):acylating agent:organic base from 1:1:1 to 1:5:5, or in a basic solvent, at molar ratio 1(S):acylating agent from 1:1 to 1:5, at 10–70° C., for 1–24 hours;

(2) hydrolysing 2(S) in an aqueous environment with an acidic resin, for 1–24 hours, thus obtaining (S)-3-acyloxy-4-hydroxybutyric acid, 3(S);

(3) converting 3(S) to (R)-3-hydroxymethyl-3-propiolactone 4(R) by treating 3(S) with a base; and (4) converting 4(R) to (R)-3-hydroxy-4-butyrolactone 1(R) in a basic environment and then acidifying to pH 3-0, or directly in an acid environment at pH 3-0, at 10–100° C., for 1–24 hours.

As regards the acylating step (1), the acylating agent is preferably an alkylsulfonyl having 1–4 carbon atoms. Mesyl is the particularly preferred alkylsulfonyl.

The organic base is preferably selected from the group consisting of pyridine, trimethylamine, lutidine and picoline and the organic aprotic solvent is selected from the group consisting of acetonitrile, chloroform and methylene chloride.

According to the preferred embodiment, the acylation is carried out at molar ratio 1(S):acylating agent:organic base of 1:1.5:1.5, at room temperature, for 5 hours.

In step (2), the acidic resin is preferably a strongly acidic resin selected from the group consisting of AMBERLITE IR 120 and AMBERLIST 15. Isolation of the resulting (S)-3-acyloxy-4-hydroxybutyric acid is not necessary.

In step (3) wherein 3(S) is converted to lactone 4(R) the treatment of 3(S) with a base is preferably carried out with an inorganic base selected from the group consisting of $NaHCO_3$, $Na_2CO_3$ and NaOH or an organic base selected from the group consisting of trimethylamine and pyridine at 10–80° C.

The lactone 4(R), (R)-3-hydroxymethyl-3-propiolactone, is a novel compound. In step (4), the conversion of 4(R) to the final lactone 1(R) is preferably carried out by alkaline hydrolysis with 3N NaOH for 30–60 minutes, preferably 45 minutes, at room temperature, and subsequent acidification with 3N HCl to pH 2 or by acidification, preferably with 2N HCl.

The process of the present invention for preparing (R)-3-hydroxy-4-butyrolactone 1(S) is illustrated in the following non-limiting example.

EXAMPLE (a) Preparation of (S)-3-mesyloxy-4-butyrolactone

A solution of (S)-3-hydroxy-4-butyrolactone (8 g; 78.36 mmoles) and anhydrous pyridine (9.3 g; 117.54 mmoles) in anhydrous $CH_2Cl_2$ (400 mL) kept under stirring was cooled in an ice-bath.

Mesyl chloride (13.464 g; 117.54 mmoles) was added to the solution dropwise. Upon addition termination, the solution was kept under stirring for 5 hours at room temperature and then washed with 5% HCl, $H_2O$ and dried on $Na_2SO_4$. To the liquid residue obtained by evaporation of the organic phase, isopropyl ether was added till complete precipitation and the resulting mixture was kept at 4° C. overnight. The residue obtained by decantation was dried under vacuum, giving 12.6 g of the title compound (89%); TLC: Silica gel, eluant=EtOAc, Rf=0.69; M.P.=81–82° C. (decomp.);

$$[\alpha]_D^{20} = -61.8°(c = 0.6, CHCl_3);$$

$^1$H NMR(CDCl$_3$, 25° C., 200 MHz) δ 5.4(m,1H), 4.5(m, 2H), 3.1(s,3H), 2.8(m,2H); values of C, H, N calculated for $C_5H_8O_5S$: C, 33.33; H, 4.47; found: C, 33.01; H, 4.21.

(b) Preparation of (R)-3-hydroxymethyl-3-propiolactone

To a mixture of (S)-3-mesyloxy-4-butyrolactone (10.6 g; 58.83 mmoles) in $H_2O$ (115 mL), 230 mL of AMBERLITE RA 120 resin (activated in acid form) were added. The resulting mixture was kept under stirring (Shaker) for 24 hours, at room temperature and the resin was filtered off washing with 550 mL $H_2O$.

NMR of a sample at this time showed the presence of (S)-4-hydroxy-3-mesyloxybutyric acid ($^1$H NMR (D$_2$O, 25° C., 200 MHz) δ 5.12(m,1H), 3.88(dd,1H), 3.75(dd,1H), 3.20 (s,3H), 2.82(d,2H)).

Following addition of $NaHCO_3$ (3.953 g; 47.06 mmoles) the solution was heated to 50° C. under stirring for 2 hours and then the water was evaporated under vacuum. The residue was taken up with EtOAc, the solid filtered off and the organic solvent evaporated. The residue was purified by flash chromatography on silica gel using hexane-EtOAc 6:4 as eluant, giving 3.31 g of (R)-3-hydroxymethyl-3-propiolactone as a colourless oil (55%); TLC: silica gel, eluant=hexane-EtOAc 6:4, Rf=0.21;

$$[\alpha]_D^{20} = -28.8°(c = 0.95, CHCl_3);$$

$^1$H NMR (CDCl$_3$, 25° C., 200 MHz) δ 4.65(m, 1H), 4.10(dd,1H), 3.80(dd,1H), 3.45(d,2H), 2.15(brs,1H); values of C,H,N calculated for $C_4H_6O_3$: C, 47.06; H, 5.92; found: C,46.75; H, 5.97.

(c) Preparation of (R)-3-hydroxy-4-butyrolactone 100 mL of 3N NaOH were added to (R)-3-hydroxymethyl-3-propiolactone (3.5 g; 34.28 mmoles) and the resulting solution was kept under stirring at room temperature for 45 minutes. 3N HCl was added to the solution up to pH=2 while cooling with an ice-bath. The residue was taken up with EtOAc, the NaCl which formed was filtered off and the organic solvent removed by evaporation under vacuum. 3.4 g (97%) of the title compound were obtained. TLC: silica gel, eluant=EtOAc, Rf=0.63;

$$[\alpha]_D^{20} = +88.2°(c = 0.8, MeOH_3);$$

$^1$H NMR (CDCl$_3$), 25° C., 200 mHz) δ 4.62(m,1H), 4.40(dd,1H), 4.28 (dm, 1H), 3.50(brs, 1H), 2.73(dd, 1H), 2.45(dm, 1H); values of C, H, N calculated for $C_4H_6O_3$: C, 47.06; H, 5.92; found: C, 46.88; H, 5.83.

$$[\alpha]_D^{20}$$

is the same as that of a sample obtained from (R)-carnitine, as described in SYNLETT, 1977, 71–74.

It will be apparent to every expert in organic synthesis that the process of the present invention overcomes the drawbacks of the known methods. In particular, the present process, also when it is conducted on an industrial scale, may comprise only three steps (exclusively for clarity's sake a 4-step process has been previously illustrated), insofar as the (S)-3-acyloxy-4-hydroxybutyric acid obtained in step (2) need not be isolated, but can rather be treated as shown in step (3). Actually, therefore, from an operating viewpoint steps (2) and (3) may be regarded as a single step.

(R)-3-hydroxy-4-butyrolactone obtained with the present process has very high optical purity. Indeed, the enantiomeric excess (ee) gas-chromatographically assessed on a chiral column is ≧98%.

As mentioned earlier, (R)-3-hydroxy-4-butyrolactone can be utilised for synthesizing important active ingredients. For instance, it is a key intermediate in the preparation of (R)-carnitine.

Such process for preparing (R)-carnitine from (S)-carnitine is as shown in the following reaction scheme:

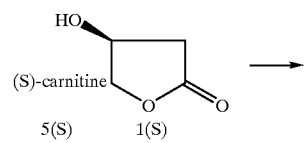

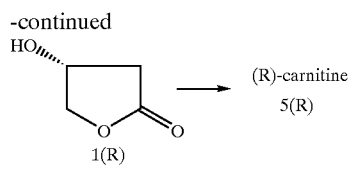

and comprises the steps of:
(a) converting (S)-carnitine inner salt, 5(S), to (S)-3-hydroxy-4-butyrolactone, 1(S), by preparing a solution of (S)-carnitine inner salt in a solvent inert to the conversion, keeping the solution thus obtained at 100–190° C., for 0.5–5 hours, and isolating 1(S) by evaporation of the solvent;
(b) converting 1(S) to (R)-3-hydroxy-4-butyrolactone 1(R); and
(c) converting 1(R) to (R)-carnitine inner salt, 5(R), via known methods;

and is characterised in that the conversion of step (b) is carried out according to the process of the present invention.

What is claimed is:

1. A process for producing (R)-3-hydroxy-4-butyrolactone according to the reaction scheme:

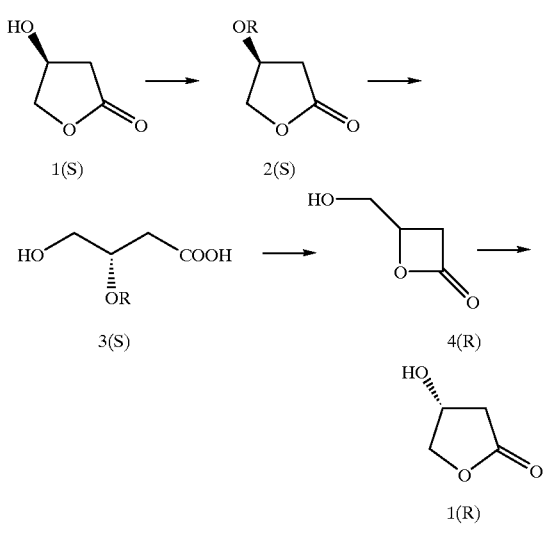

which comprises the steps of:
(1) acylating (S)-3-hydroxy-4-butyrolactone, 1(S), to (S)-3-acyloxy-4-butyrolactone, 2(S), wherein —OR is a leaving group wherein R is a group selected from alkylsulfonyl having 1–12 carbon atoms, arylsulfonyl, formyl and trifluoroacetyl, by reacting 1(S) with an acylating agent selected from an acyl halogenide RY and an anhydride R—O—R wherein Y is halogen, preferably chlorine, and R is as previously defined, optionally in the presence of an organic base consisting of a tertiary amine, in an aprotic organic solvent, at molar ratio 1(S):acylating agent:organic base from 1:1:1 to 1:5:5, or in a basic solvent, at molar ratio 1(S):acylating agent from 1:1 to 1:5, at 10–70° C., for 1–24 hours;
(2) hydrolysing 2(S) in an aqueous environment with an acidic resin, for 1–24 hours, thus obtaining (S)-3-acyloxy-4-hydroxybutyric acid, 3(S);
(3) converting 3(S) to (R)-3-hydroxymethyl-3-propiolactone 4(R) by treating 3(S) with a base; and (4) converting 4(R) to (R)-3-hydroxy-4-butyrolactone 1(R) in a basic environment and then acidifying to pH 3–0, or directly in an acid environment at pH 3–0, at 10–100° C., for 1–24 hours.

2. The process for claim 1, wherein the alkylsulfonyl has 1–4 carbon atoms.

3. The process of claim 2, wherein the alkylsulfonyl is mesyl.

4. The process of claim 1, wherein in step (1) the organic base is selected from the group consisting of pyridine, trimethylamine, lutidine, and picoline and the organic aprotic solvent is selected from the group consisting of acetonitrile, chloroform and methylene chloride.

5. The process of claim 1, wherein the acylation is carried out at molar ratio 1(S):acylating agent:organic base of 1:1.5:1.5, at room temperature, for 5 hours.

6. The process for claim 1, wherein the acidic resin of step (2) is a strongly acidic resin selected from the group consisting of AMBERLITE IR 120 and AMBERLIST 15.

7. The process of claim 1, wherein treatment of 3(S) with a base is carried out with an inorganic base selected from the group consisting of $NaHCO_3$, $Na_2CO_3$ and NaOH or organic base selected from the group consisting of trimethylamine and pyridine, at 10–80° C.

8. The process of claim 1, wherein the conversion of 4(R) to 1(R) of step (4) is carried out by alkaline hydrolysis with NaOH, for 0.5–24 hours, at 10–100° C., and subsequent acidification.

9. The process of claim 8, wherein the conversion of step (4) is carried out by alkaline hydrolysis with 3N NaOH for 30–60 minutes, preferably 45 minutes, at room temperature, and subsequent acidification with 3N HCl to pH 2.

10. The process of claim 1, wherein the conversion of 4(R) to 1(R) is carried out by acid hydrolysis with HCl for 1–24 hours, at 10–100° C.

11. The process of claim 10, wherein the conversion of step (4) is carried out by acidification with 2N HCl to pH2 for 1–3 hours, preferably 2 hours, at 50° C.

12. (R)-3-hydroxymethyl-3-propiolactone.

13. A process for preparing (R)-carnitine from (S)-carnitine according to the following reaction scheme:

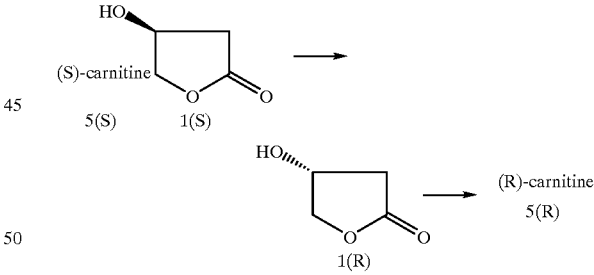

which comprises the steps of:
(a) converting (S)-carnitine inner salt, 5(S), to (S)-3-hydroxy-4-butyrolactone, 1(S), via known methods;
(b) converting 1(S) to (R)-3-hydroxy-4-butyrolactone 1(R); and
(c) converting 1(R) to (R)-carnitine inner salt, 5(R) via known methods, characterised in that the conversion of step (b) is carried out by the process of claims 1–9.

14. The process of claim 11, wherein the step (a) of conversion from 5(S) to 1(S) comprises preparing a solution of (S)-carnitine inner salt with a solvent inert to the conversion, keeping the solution thus obtained at 100–190° C., for 0.5–5 hours, and isolating 1(S) by evaporation of the solvent.

15. The process of claim 1, wherein said (R)-3-hydroxy-4-butyrolactone is produced in an enantiomeric excess (ee) of ≧98%, as assessed by gas chromatography on a chiral column.

16. The process of claim 1, wherein in step (1), Y is chlorine.

* * * * *